United States Patent
Koller et al.

(10) Patent No.: US 8,318,496 B2
(45) Date of Patent: Nov. 27, 2012

(54) COMPOUNDS AND METHODS FOR IMPROVING CELLULAR UPTAKE OF OLIGOMERIC COMPOUNDS

(75) Inventors: Erich Koller, Carlsbad, CA (US); C. Frank Bennett, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 40 days.

(21) Appl. No.: 12/681,593

(22) PCT Filed: Oct. 6, 2008

(86) PCT No.: PCT/US2008/078956
§ 371 (c)(1),
(2), (4) Date: Jul. 30, 2010

(87) PCT Pub. No.: WO2009/046426
PCT Pub. Date: Apr. 9, 2009

(65) Prior Publication Data
US 2010/0292304 A1  Nov. 18, 2010

Related U.S. Application Data

(60) Provisional application No. 60/977,598, filed on Oct. 4, 2007.

(51) Int. Cl.
*C12N 15/00* (2006.01)
*C12Q 1/68* (2006.01)
*A01N 63/00* (2006.01)
*A01N 43/04* (2006.01)
*C07H 21/02* (2006.01)
*C07H 21/00* (2006.01)

(52) U.S. Cl. ............ 435/455; 435/6; 424/93.2; 514/55; 536/24.5; 536/23.1

(58) Field of Classification Search .................. None
See application file for complete search history.

(56) References Cited

U.S. PATENT DOCUMENTS

| 7,884,086 B2 | 2/2011 | Bennett et al. | |
| 2003/0143732 A1* | 7/2003 | Fosnaugh et al. | 435/325 |
| 2008/0015162 A1 | 1/2008 | Bhanot et al. | |

FOREIGN PATENT DOCUMENTS

| WO | WO 2004/090105 | 10/2004 |
| WO | WO 2007/143315 | 12/2007 |

OTHER PUBLICATIONS

Koller, E., et al. (2011). "Mechanisms of single-stranded phosphorothioate modified antisense oligonucleotide accumulation in hepatocytes". Nucleic Acids Research v.39(11):4795-4807.*
Bennett et al., "Cationic Lipids Enhance Cellular Uptake and Activity of Phosphorothioate Antisense Oligonucleotides" Molecular Pharmacology (1992) 41:1023-1033.
Crooke, "Oligonucleotide therapy" Current Opinion in Biotechnology (1992) 3:656-661.
Crooke, "In vitro toxicology and pharmacokinetics of antisense oligonucleotides" Anti-cancer Drug Design (1991) 6:609-646.
Hussain et al., "A novel anionic dendrimer for improved cellular delivery of antisense oligonucleotides" Journal of Controlled Release (2004) 99(1):139-155.
Krieg et al., "Uptake of Oligodeoxyribonucleotides by Lymphoid Cells is Heterogeneous and Inducible" Antisense Research and Development (1991) 1(2):161-171.
Nestle et al., "Cationic lipid is not required for uptake and selective inhibitory activity of ICAM-1 phosphorothioate antisense oligonucleotides in keratinocytes" Journal of Investigative Dermatology (1994) 103(4):569-575.
Ruther et al., "Inducible Formation of Liver Tumors in Transgenic Mice" Oncogene (1993) 8(1):87-93.
Shoji et al., "Mechanism of Cellular Uptake of Modified Oligodeoxynucleotides Containing Methylphosphonate Linkages" Nucleic Acids Research (1991) 19(20):5543-5550.
Takakura et al., "Uptake characteristics of oligonucleotides in the isolated rat liver perfusion system" Antisense and Nucleic Acid Drug Development (1996) 6(3):177-183.
International Search Report for application PCT/US2008/078956 dated Aug. 21, 2009.

* cited by examiner

*Primary Examiner* — Jennifer Pitrak McDonald
(74) *Attorney, Agent, or Firm* — Knobbe, Martens, Olson & Bear, LLP

(57) ABSTRACT

The present invention provides method of optimizing the efficacy and potency of antisense drugs. In certain embodiments, the invention provides assays useful for determining favorable oligonucleotide characteristics and excipeints for improved cellular uptake.

10 Claims, No Drawings

US 8,318,496 B2

COMPOUNDS AND METHODS FOR IMPROVING CELLULAR UPTAKE OF OLIGOMERIC COMPOUNDS

RELATED APPLICATIONS

This application is a 35 U.S.C. §371 national phase application of international application Ser. No. PCT/US2008/078956, filed on Oct. 6, 2008, which is a non-provisional of U.S. patent application Ser. No. 60/977,598, filed on Oct. 4, 2007, the disclosure of each of which is incorporated herein by reference in its entirety.

FIELD OF THE INVENTION

The present invention provides a method of optimizing the efficacy and potency of antisense drugs. This method is achieved by implementing assays described herein useful for determining favorable oligonucleotide characteristics for cellular uptake.

BACKGROUND OF THE INVENTION

There are desirable molecular targets for drug discovery that are considered "undruggable" by traditional small molecule technology. Such targets are often members of families of closely related proteins that are too similar in structure for traditional drugs to distinguish amongst, the biological function of the protein is unknown, or it is difficult to develop an assay for drug screening. Antisense drugs discriminate between targets based on their genetic sequence, so certain such "undruggable" targets may be amenable to antisense.

SUMMARY OF THE INVENTION

In certain embodiments, the present invention provides methods comprising contacting a cell with a reporter oligomeric compound and a competitor oligomeric compound and detecting antisense activity of the reporter oligomeric compound.

In certain embodiments, the present invention provides methods comprising preparing two or more test samples wherein each test sample comprises a cell, a concentration of a reporter oligomeric compound, and a concentration of a competitor oligomeric compound, wherein;

the concentration of the reporter oligomeric compound is the same in each of the two or more test samples and the concentration of the competitor oligomeric compound is different in each of the two or more test samples or the concentration of the reporter oligomeric compound is different in each two or more test samples and the concentration of the competitor oligomeric compound is different in each of the two or more test samples; and detecting antisense activity of the reporter oligomeric compound in each of the two or more test samples.

In certain such embodiments, the concentration of the reporter oligomeric compound is the same in each of the two or more test samples and the concentration of the competitor oligomeric compound is different in each of the two or more test samples.

In certain such embodiments, the concentration of the reporter oligomeric compound is different in each two or more test samples and the concentration of the competitor oligomeric compound is different in each of the two or more test sample.

In certain embodiments, the invention provides methods of assessing the relative uptake of a first and a second competitor oligomeric compounds comprising:

preparing two or more first test samples wherein each first test sample comprises a cell, a concentration of a reporter oligomeric compound, and a concentration of a first competitor oligomeric compound, wherein;

the concentration of the reporter oligomeric compound is the same in each of the two or more first test samples and the concentration of the first competitor oligomeric compound is different in each of the two or more first test samples or the concentration of the reporter oligomeric compound is different in each two or more first test samples and the concentration of the first competitor oligomeric compound is different in each of the two or more first test samples;

preparing two or more second test samples wherein each second test sample comprises a cell, a concentration of the reporter oligomeric compound, and a concentration of a second competitor oligomeric compound, wherein;

the concentration of the reporter oligomeric compound is the same in each of the two or more second test samples and the concentration of the second competitor oligomeric compound is different in each of the two or more second test samples or the concentration of the reporter oligomeric compound is different in each two or more second test samples and the concentration of the second competitor oligomeric compound is different in each of the two or more second test samples;

detecting antisense activity of the reporter oligomeric compound in each of the two or more first test samples and each of the two or more second test samples; and thereby assessing relative uptake of the first and second competitor oligomeric compound.

In certain such embodiments, the concentration of the reporter oligomeric compound is different in each of the two or more first test samples and in each of the two or more second test samples and the concentration of the first competitor oligomeric compound is different in each of the two or more first test samples and the concentration second competitor oligomeric compound is different in each of the two or more test samples.

In certain embodiments, the concentrations of first competitor oligomeric compound in the first test samples are the same as the concentrations of the second competitor oligomeric compound in the second test samples.

In certain embodiments, the concentration of the reporter oligomeric compound is the same in each of the two or more first test samples and in each of the two or more second test samples and the concentration of the first competitor oligomeric compound is the same in each of the two or more first test samples and the concentration second competitor oligomeric compound is the same in each of the two or more test samples.

In certain embodiments, the concentration of first competitor oligomeric compound in the first test samples is the same as the concentration of the second competitor oligomeric compound in the second test samples.

In certain embodiments, the cell is a hepatocyte; a primary hepatocyte, or MHT cell.

In certain embodiments, the contacting occurs in the absence of cationic lipid.

In certain embodiments, the contacting occurs in the presence of dextran sulfate.

In certain embodiments, the present invention provides methods for assessing cellular uptake of an oligomeric compound comprising contacting an MHT cell with the oligomeric compound in the absence of cationic lipid.

In certain embodiments, the present invention provides kits comprising cells, and one or more oligomeric compounds. In certain such embodiments, the cells are MHT cells.

In certain embodiments, the present invention provides formulations comprising an antisense oligomeric compound and an excipient, wherein the excipient saturates a mechanism of unproductive accumulation in a cell. In certain such embodiments, the excipient comprises an oligomeric compound. In certain embodiments, the oligomeric compound of the excipient is not an antisense oligomeric compound.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

As used herein, the term "nucleoside" means a glycosylamine comprising a nucleobase and a sugar. Nucleosides include, but are not limited to, naturally occurring nucleosides, abasic nucleosides, modified nucleosides, and nucleosides having mimetic bases and/or sugar groups.

As used herein, the term "nucleobase" refers to the base portion of a nucleoside. A nucleobase may comprise any atom or group of atoms capable of hydrogen bonding to a base of another nucleic acid.

As used herein, the term "deoxyribonucleotide" means a nucleotide having a hydrogen at the 2' position of the sugar portion of the nucleotide. Deoxyribonucleotides may be modified with any of a variety of substituents.

As used herein, the term "ribonucleotide" means a nucleotide having a hydroxy at the 2' position of the sugar portion of the nucleotide. Ribonucleotides may be modified with any of a variety of substituents.

As used herein, the term "oligomeric compound" refers to a polymeric structure comprising two or more sub-structures and capable of hybridizing to a region of a nucleic acid molecule. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

As used herein, the term "reporter oligomeric compound" refers to an oligomeric compound that that is at least partially complementary to and capable of hybridizing with a target nucleic acid molecule, wherein if hybridization occurs, some detectable change results. In certain embodiments, hybridization of a reporter oligomeric compound to its target nucleic acid molecule modulates (increases or decreases) expression of a target nucleic acid, resulting in more or less target protein. In certain such embodiments, the presence or amount of target protein is detectable and/or measurable. In certain embodiments, hybridization of a reporter oligomeric compound to a target nucleic acid is detectable by Northern Blot, by fluorescence or by the presence of a splice variant that would not be present or would be present at a different amount in the absence of hybridization of the reporter oligomeric compound with its target nucleic acid molecule. Reporter oligomeric compounds include, but are not limited to, compounds that are oligonucleotides, oligonucleosides, oligonucleotide analogs, oligonucleotide mimetics, and chimeric combinations of these. In certain embodiments, a reporter oligomeric compound comprises an oligonucleotide linked to a conjugate. In certain embodiments, the reporter oligomeric compound comprises a sequence or motif the cellular uptake of which is to be assessed.

The term "competitor oligomeric compound" refers to an oligomeric compound that is not identical to and does not hybridize with the reporter oligomeric compound. In certain embodiments, the competitor oligomeric compound comprises a sequence or motif the cellular uptake of which is to be assessed.

As used herein, the term "oligonucleotide" refers to an oligomeric compound comprising a plurality of linked nucleosides. In certain embodiment, one or more nucleosides of an oligonucleotide is modified. In certain embodiments, an oligonucleotide comprises ribonucleic acid (RNA) or deoxyribonucleic acid (DNA). In certain embodiments, oligonucleotides are composed of naturally- and/or non-naturally-occurring nucleobases, sugars and covalent internucleoside linkages, and may further include non-nucleic acid conjugates.

As used herein "oligonucleoside" refers to an oligonucleotide in which the internucleoside linkages do not contain a phosphorus atom.

As used herein "internucleoside linkage" refers to a covalent linkage between adjacent nucleosides.

As used herein, the term "antisense compound" refers to an oligomeric compound that is at least partially complementary to a target nucleic acid molecule to which it hybridizes. In certain embodiments, an antisense compound modulates (increases or decreases) expression of a target nucleic acid. Antisense compounds include, but are not limited to, compounds that are oligonucleotides, oligonucleosides, oligonucleotide analogs, oligonucleotide mimetics, and chimeric combinations of these. Consequently, while all antisense compounds are oligomeric compounds, not all oligomeric compounds are antisense compounds.

As used herein, the term "antisense activity" refers to any detectable and/or measurable activity attributable to the hybridization of an antisense compound to its target nucleic acid. Such detection and or measuring may be direct or indirect. For example, in certain embodiments, antisense activity is assessed by detecting and or measuring the amount of target protein. In certain embodiments, antisense activity is assessed by detecting and/or measuring the amount of target nucleic acids and/or cleaved target nucleic acids and/or alternatively spliced target nucleic acids.

As used herein the term "detecting antisense activity" or "measuring antisense activity" means that a test for detecting or measuring antisense activity is performed on a particular sample and compared to that of a control sample. Such detection and/or measuring may include values of zero. Thus, if a test for detection of antisense activity results in a finding of no antisense activity (antisense activity of zero), the step of "detecting antisense activity" has nevertheless been performed.

As used herein the term "control sample" refers to a sample that has not been contacted with a reporter oligomeric compound.

As used herein, the term "various concentrations" or "different concentrations" can include concentrations of zero. Thus, the statement that an assay component was tested at various concentrations may include samples where that component is absent.

As used herein, the term "uptake" or "taken up" refers to the ability of an oligomeric compound to enter a cell in a way that allows antisense activity.

As used herein, the term "accumulate" refers to the ability of an oligomeric compound to enter a cell, whether or not it is available for antisense activity. For example, if an oligomeric compound enters a cell, but is localized such that it is shielded from its target nucleic acid and no antisense activity is detected, the oligomeric compound has "accumulated" in the cell, but has not been "taken up."

As used herein, the term "antisense oligonucleotide" refers to an antisense compound that is an oligonucleotide.

As used herein, the term "test sample" refers to a sample suitable for testing and includes, but is not limited to samples in wells of multiwell plates, petri dishes, test tubes, or assay kits.

As used herein, the term "motif" refers to a pattern of unmodified and modified nucleosides and/or linkages in an oligomeric compound. In certain embodiments, a motif can be described using a shorthand nomenclature comprising a series of numbers where each number represents the number of nucleosides of an oligomeric compound comprising a particular modification, where the first number represents the number of nucleosides of a type starting at the 5' end of the oligomeric compound. For example: a 2-8-3 MOE-DNA gapmer is an oligonucleotide wherein the two 5' terminal nucleosides are MOE-substituted nucleosides, the next eight nucleosides are unsubstituted DNA, and the three 3' terminal nucleosides are MOE-substituted nucleosides. Linkage modifications can likewise be identified, for example the above 2-8-3 MOE gapmer could also have a 3-2-3-2-2 alternating phosphorothioate/phosphodiester, mixed backbone, wherein the first three linkages starting at the 5' end (i.e., the linkages between the first and second nucleoside, the second and third nucleoside, and the third and fourth nucleoside) are each phosphorothioate, the next two are phosphodiester, the next three are phosphorothioate, the next two are phosphodiester, and the final two are phosphorothioate.

As used herein, the term "target protein" refers to a protein, the modulation of which is desired or which is suitable for testing.

As used herein, the term "target gene" refers to a gene encoding a target protein.

As used herein, the terms "target nucleic acid" refers to any nucleic acid molecule the expression or activity of which is capable of being modulated by an antisense compound or a reporter oligomeric compound, including endogenous and exogenously introduced nucleic acids. Target nucleic acids include, but are not limited to, RNA (including, but not limited to pre-mRNA and mRNA or portions thereof) transcribed from DNA encoding a target, and also cDNA derived from such RNA, and miRNA. For example, the target nucleic acid can be a cellular gene (or mRNA transcribed from the gene) whose expression is associated with a particular disorder or disease state, or a nucleic acid molecule from an infectious agent.

As used herein, the term "nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

As used herein, the term "non-complementary nucleobase" refers to a pair of nucleobases that do not form hydrogen bonds with one another or otherwise support hybridization.

As used herein, the term "complementary" refers to the capacity of an oligomeric compound to hybridize to another oligomeric compound or nucleic acid through nucleobase complementarity. In certain embodiments, an antisense compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, the term "specifically hybridizes" refers to the ability of an oligomeric compound to hybridize to one nucleic acid site with greater affinity than it hybridizes to another nucleic acid site. In certain embodiments, an antisense oligonucleotide specifically hybridizes to more than one target site. As used herein, the term "expression" refers to all the functions and steps by which a gene's coded information is converted into structures present and operating in a cell. Such structures include, but are not limited to the products of transcription and translation.

As used herein, the term "2'-modified" or "2'-substituted" means a sugar comprising substituent at the 2' position other than H or OH. 2'-modified monomers, include, but are not limited to, BNA's and monomers (e.g., nucleosides and nucleotides) with 2'-substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N($R_m$)($R_n$), or O—$CH_2$—C(=O)—N($R_m$)($R_n$), where each $R_m$ and $R_n$ is, independently, H or substituted or unsubstituted $C_1$-$C_{10}$ alkyl. In certain embodiments, oligomeric compounds comprise a 2'modified monomer that does not have the formula 2'-O$(CH_2)_nH$, wherein n is one to six. In certain embodiments, oligomeric compounds comprise a 2'modified monomer that does not have the formula 2'-$OCH_3$. In certain embodiments, oligomeric compounds comprise a 2'modified monomer that does not have the formula or, in the alternative, 2'O$(CH_2)_2$ $OCH_3$.

As used herein, the term "bicyclic nucleic acid" or "BNA" or "bicyclic nucleoside" or "bicyclic nucleotide" refers to a nucleoside or nucleotide wherein the furanose portion of the nucleoside includes a bridge connecting two carbon atoms on the furanose ring, thereby forming a bicyclic ring system.

As used herein, unless otherwise indicated, the term "methyleneoxy BNA" alone refers to β-D-methyleneoxy BNA.

As used herein, the term "MOE" refers to a 2'-O-methoxyethyl substituent.

As used herein, the term "gapmer" refers to a chimeric oligomeric compound comprising a central region (a "gap") and a region on either side of the central region (the "wings"), wherein the gap comprises at least one modification that is different from that of each wing. Such modifications include nucleobase, monomeric linkage, and sugar modifications as well as the absence of modification (unmodified). Thus, in certain embodiments, the nucleotide linkages in each of the wings are different than the nucleotide linkages in the gap. In certain embodiments, each wing comprises nucleotides with high affinity modifications and the gap comprises nucleotides that do not comprise that modification. In certain embodiments the nucleotides in the gap and the nucleotides in the wings all comprise high affinity modifications, but the high affinity modifications in the gap are different than the high affinity modifications in the wings. In certain embodiments, the modifications in the wings are the same as one another. In certain embodiments, the modifications in the wings are different from each other. In certain embodiments, nucleotides in the gap are unmodified and nucleotides in the wings are modified. In certain embodiments, the modification(s) in each wing are the same. In certain embodiments, the modification(s) in one wing are different from the modification(s) in the other wing. In certain embodiments, oligomeric antisense compounds are gapmers having 2'-deoxynucleotides in the gap and nucleotides with high-affinity modifications in the wing.

As used herein, the term "cap structure" or "terminal cap moiety" refers to chemical modifications, which have been incorporated at either terminus of an antisense compound.

B. Cellular Uptake of Oligomeric Compounds

Oligomeric compounds designed to hybridize to specific mRNA sequences have been used to inhibit the function of a number of cellular and viral proteins. Thus, if the DNA sequence of a protein of interest is known, it is possible to design complementary oligomeric compounds that bind the target RNA and inhibit expression of the protein. Unmodified oligo-deoxyribonucleotides have been used to inhibit the expression of several viral and cellular encoded proteins in cell culture. However, these compounds are unstable in biological fluids and display poor cellular uptake characteristics (Bennett et al., *Molecular Pharmacology*, 41, 1023 (1992)). Cellular uptake of unmodified oligo-deoxynucleotides is poorly understood, but appears to involve binding to acceptor sites on a tissue surface responsible for facilitating uptake (Crooke S. T., *Antisense Drug Technology*, Second Ed. (2008), Chapter 6, CRC Press, Florida).

To address uptake limitations, numerous modifications of the oligonucleotide phosphodiester backbone have been performed to decrease the sensitivity of the oligonucleotides to nucleases and/or to increase cellular uptake. Examples of such chemistry modifications include, for example, phosphorothioates and 2'-methoxyethyl (2'MOE) (Bennett et al., *Molecular Pharmacology*, 41, 1023 (1992).

It is known that uptake varies according to oligonucleotide type (Crooke, S. T., *Current Opinion in Biotechnology*, 3, 656 (1992)). For example, the data suggest that phosphorothioate oligonucleotides are taken up by receptor-mediated endocytosis. Localization studies using fluorescently labeled oligonucleotides support this notion (Crooke, S. T., *Current Opinion in Biotechnology*, 3, 656 (1992)).

Uptake affects the pharmacological activity of oligomeric compounds. Pharmacological activity depends on a number of factors that influence the effective concentration of these agents at specific nuclear or cytoplasmic receptors. A key factor is the ability of antisense compounds to traverse the plasma membrane of specific cells involved in disease processes (Crooke, R. M., *Anti-cancer Drug Design*, 6, 609 (1992)).

In certain embodiments, the present invention provides methods for determining favorable characteristics for cellular uptake. Variables such as chemical modifications and sequence may affect cellular uptake. It is advantageous to ascertain the particular characteristics favored by a cell in order to optimize cellular uptake. By optimizing cellular uptake, the efficacy and potency of antisense drugs can be increased.

C. Certain Cells

In certain embodiments, the present invention provides cells useful for assessing uptake of oligomeric compounds. Many mammalian cell lines accumulate oligomeric compounds when such oligomeric compounds are added to culture media. However, in those cultured cell lines, antisense oligomeric compounds typically do not demonstrate antisense activity, perhaps resulting from localization within the cells that prevents the antisense oligomeric compounds from contacting their target nucleic acids. To observe and test antisense activity in cell lines, investigators typically must add cationic lipids. See e.g., Bennett et al., Molecular Pharmacology, 41: 1023-1033(1992). In vivo, though, administration of antisense oligomeric compounds in only saline has produced sequence specific antisense activity. Thus, it appears that there is a difference between uptake of oligomeric compounds in cell lines and in cells in vivo. Accordingly, it is difficult to assess, for example, the effect of different sequences, chemical modifications, or motifs on uptake of oligomeric compounds, since assays using cell lines are not expected to yield meaningful results.

In certain embodiments, the present invention provides primary cells that demonstrate antisense activity when antisense oligomeric compounds are added without cationic lipids. In certain embodiments, such cells are hepatocytes, macrophages, or keratinocytes. In certain embodiments, such cells are primary liver cells. In certain embodiments, cells are primary hepatocytes. In certain embodiments, such cells are mouse or human primary hepatocytes. In certain embodiments, primary hepatocytes are useful for assessing uptake of oligomeric compounds for up to 24 hours. In certain embodiments, primary hepatocytes are useful for assessing uptake of oligomeric compounds for up to 48 hours. In certain embodiments, primary hepatocytes lose their ability to demonstrate antisense activity after about 24 to 30 hours. Certain such uses of primary hepatocytes may be found, for example, in U.S. patent application Ser. No. 11/221,001, which is hereby incorporated by reference in its entirety for any and all purposes.

In certain embodiments, the present invention provides a cell line that is useful for assessing uptake of oligomeric compounds. In certain embodiments, the invention provides a hepatocellular carcinoma cell line derived from a primary tumor that retains the ability to uptake oligomeric compounds. In certain such embodiments, the cell line is derived from an SV40 large T antigen tumor. In certain embodiments, the cell line is derived from a mouse. In certain embodiments, the cell line is MHT. In certain embodiments, such MHT cells retain the ability to uptake oligomeric compounds for 20 or more passages. In certain embodiments, such cells demonstrate antisense activity when contacted with an antisense oligomeric compound. In certain embodiments, such cells are contacted with a reporter oligomeric compound and antisense activity is detected and/or measured.

D. Certain Assays

In certain embodiments, the invention provides assays for assessing uptake of oligomeric compounds. In certain embodiments, such assays involve (1) plating cells, for example MHT cells, on a multiwell plate (2) adding varying concentrations of a reporter oligomeric compound or no oligomeric compound to each plate, and (3) detecting antisense activity. In certain embodiments, such an assay can be performed in parallel with several reporter oligomeric compounds. For example, the several reporter oligomeric compounds may have the same sequence, but differ in type, number or position of chemical modifications or in length or presence or type of conjugate group. Or the such several reporter oligomeric compounds may have the same target nucleic acid, but different sequences. Thus, in certain embodiments, the invention provides ways of comparing oligomeric compounds.

In certain embodiments, the invention provides a competition assay useful for assessing uptake of oligomeric compounds. In certain such embodiments, (1) cells, for example MHT cells, are plated on a multiwell plate; (2) a competitor oligomeric compound is added to each plate at the same concentration per well; (3) a reporter oligomeric compound is added to each of several wells, typically at several different concentrations; and (4) antisense activity is detected and/or measured. In certain embodiments, such assays are useful for assessing the relative uptake of the reporter oligomeric compound and the competitor oligomeric compound. In certain embodiments, the concentration of the competitor oligomeric compound is varied and the concentration of the reporter oligomeric compound is the same for each well. In certain embodiments, two or more competitor oligomeric compounds are separately tested against the same reporter oligomeric compound to assess the relative uptake of the two or more competitor oligomeric compounds. In certain embodiments, two or more reporter oligomeric compounds are used and the antisense activity of each of them is measured. In such embodiments, the assay may or may not include a competitor oligomeric compound. One of ordinary skill in the art will readily appreciate that these components can be manipulated in a variety of ways.

E. Certain Oligomeric Compounds

As described above, in certain embodiments, the invention provides assays for determining relative uptake of oligomeric compounds. Such assays are useful for generating a structure activity relationship to better design oligomeric compounds for use in vivo, including therapeutic uses. Accordingly, the oligomeric compounds suitable for assays of the present invention may comprise any known or newly designed chemical modifications including, without limitation, nucleoside modifications, including sugar modifications and base modifications, and modified internucleoside linkages, including oligomeric compounds with mixed backbones. Also suitable for testing in assays of the present invention are the effects of various caps, conjugates or terminal groups. Also suitable for testing in assays of the present invention are motifs varying the type, number and/or position of chemical modifications. Examples of motifs include, but are not limited to, gapmers, hemimers, blockmers, alternating and positional motifs all with any number and/or type of modifications in the various regions. Certain modifications and motifs suitable for oligomeric compounds for use in the assays of the present invention may be found, for example, in pending U.S. application Ser. No. 11/745,429; PCT/US2007/068404; and U.S. application Ser. No. 11/221,001, which are incorporated by reference in their entirety. Also suitable for testing in assays of the present invention are oligomeric compounds of differing lengths. Assays of the present invention may also be used to assess whether similarly modified oligomeric compounds with different sequences are preferentially taken up. Such modifications and combinations of modifications may be incorporated into one or more reporter oligomeric compound and/or one or more competitor oligomeric compound.

In certain embodiments, the present invention provides oligomeric compounds of any of a variety of ranges of lengths. In certain embodiments, the invention provides oligomeric compounds comprising oligonucleotides consisting of X to Y linked nucleosides, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that $X \leq Y$. For example, in certain embodiments, the invention provides oligomeric compounds, including, but not limited to reporter oligomeric compounds and competitor oligomeric compounds, which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22,21 to 23,21 to 24,21 to 25,21 to 26,21 to 27,21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

In certain embodiments, in assays using more than one oligomeric compound, the modifications, motifs, lengths, and sequences of each oligomeric compound is independent of those features of the other oligomeric compounds in the assay. In certain assays using more than one oligomeric compound, certain of those features or sets of those features are matched. Thus, for example, in certain embodiments oligomeric compounds used in an assay all have the same length and types and number of modification, but have different motifs (i.e., the modifications are differently positioned on the oligomeric compounds).

F. Certain Excipients For Administration of Oligomeric Compounds

In certain embodiments, the invention further provides excipients predicted to be useful for administration of oligomeric compounds in vivo. When certain uptake assays described above are performed in the presence of low concentrations of dextran sulfate, cellular accumulation of oligomeric compound is inhibited, but antisense activity is unchanged. This result suggests that there are two mechanisms by which oligomeric compounds accumulate in cells: a mechanism that results in unproductive accumulation and which is sensitive to low concentrations of dextran sulfate; and a productive mechanism that results in antisense activity and which is not sensitive to low concentrations of dextran sulfate. Moreover, the bulk of the oligomeric compound appears to enter the unproductive mechanism. When assays are performed in the presence of chloroquine and separately in the presence of brefeldin A, antisense activity is inhibited. These data suggest that the productive uptake mechanism is "endocytotic-like," since those compounds interfere with such processes.

Accordingly, in certain embodiments, the present invention provides excipients and formulations designed to take advantage of productive uptake and/or avoid unproductive accumulation. In certain embodiments, the invention provides formulations of antisense oligomeric compounds for administration comprising additional components that saturate the unproductive mechanism. In certain such embodiments, an additional component is one or more additional oligomeric compounds. In certain embodiments, such additional oligomeric compounds comprises different characteristics (modifications, motifs, length) such that the antisense oligomeric compound preferentially exploits the productive pathway, while the additional oligomeric compounds preferentially enter the unproductive pathway. In certain such embodiments, the additional oligomeric compounds are nonsense compounds (i.e., is not complementary to any known cellular sequence). Such excipients may be administered separately or together with an antisense oligomeric compound. If administered separately they may administered through the same route of administration or through different routes of administration. They may be administered at the same time or at different times. In certain embodiments, the excipient is first administered and the antisense oligomeric compound is later administered. Such administration includes, but is not limited to administration to an animal, including, but not limited to a human.

In certain embodiments, the invention provides assays useful for identifying such excipients. In certain instances, an excipient is an oligomeric compound. In such instances, a competition assay described above may be performed where one or more candidate excipient oligomeric compounds may be tested for its ability to increase uptake of another oligomeric compound. In such embodiments, the candidate excipient oligomeric compound may be either the competitor oligomeric compound or the reporter oligomeric compound. In certain instances an excipient is not an oligomeric compound. In such instances, one may perform an assay similar to the competition assay described above, but where the competitor oligomeric compound is replaced with a non-oligomeric candidate excipient.

G. Kits, Research Reagents And Diagnostics

The cells and assays provided herein can be utilized as research reagents and kits. For use in kits, either alone or in combination with other compounds or reagents, cells and oligomeric compounds of the present invention can be used as tools useful for studying uptake and intracellular trafficking of oligomeric compounds.

Nonlimiting Disclosure And Incorporation By Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

EXAMPLES

Example 1

Development and Characterization of MHT Cells

Transgenic mice engineered to express the SV40 large T antigen (SV40 t/T mice) under the control of the liver-specific C-reactive protein promoter are a source of transformed cells (Ruther et al., Oncogene, 8, 1993, 87-93). The expression of SV40 large T antigen can be transiently induced by injection of bacterial lipopolysaccacharide. The cells can be isolated from the livers of the transgenic mice. The cells are herein referred to as Mouse Hepatocyte SV40 T-Antigen expressing cells, or MHT cells.

Transgenic mice were anesthetized, and perfusion into the portal vein of the liver was performed to introduce collagenase into the liver tissue. The livers were isolated from the livers of SV40 t/T mice, the tissue was gently homogenized and a hepatocyte cell fraction was isolated. The cells were then placed in 12-well plates, with and without a collagen coating. The culture medium was either DMEM containing 10% fetal bovine serum (FBS) or William's Medium E containing 10% FBS, 10 mM HEPES, and glutamine. The culture medium was changed every 3 days, and any growing cells were transferred to 6-well culture plates for continued culture and expansion. Distinct populations of cells were present after approximately one month of culture. SV40 mRNA expression was monitored using real-time PCR with primers specific for SV40 mRNA; cells expressing the SV40 mRNA were identified as MHT cells.

Two groups of MHT cells, one group cultured in DMEM and the other group cultured in William's Medium E, were selected for single-cell cloning. Cells were diluted and placed into wells of a 96-well collagen-coated culture plate such that no more than one cell would be in a single well. Cells were allowed to expand. Several clones were selected and found to express SV40 mRNA, as measured by real-time PCR.

Example 2

Lipid-mediated Transfection of Oligomeric Compounds Into MHT Cells

A representative MHT cell clone was evaluated for its ability to internalize oligonucleotide in the presence of a transfection reagent. Oligomeric compounds having a nucleobase sequence complementary to SV40 mRNA were introduced into MHT cells using a lipofection:oligomeric compound ratio of 3 ug/mL:100 nM. Oligomeric compound concentrations were 25, 50, 100, or 200 nM. An untreated sample served as a control. After 48 hours, RNA was isolated from the cells and SV40 mRNA was measured by real-time PCR. The oligonucleotides were able to significantly reduce SV40 mRNA in a concentration dependent manner. SV40 mRNA was reduced by at least 60% at concentrations of 50 nM.

An oligomeric compound having a nucleobase sequence to an endogenous target was also tested, and was found to reduce target mRNA in a concentration-dependent manner at doses of 50, 100, and 200 nM.

Example 3

Oligomeric Compound Uptake In the Absence of Transfection Reagent

A representative MHT cell clone was evaluated for its ability to internalize oligomeric compounds in the absence of a transfection reagent. The endogenous target tested in lipofectin-mediated transfection (Example 2) was again tested without a transfection reagent. Cells were plated in collagen-coated 96-well plates at a density of 5000 cells per well. After one day in culture, cells were washed with phosphate-buffered saline (PBS), then overlaid with William's E Medium containing 1% FBS, 0.1% bovine serum albumin (BSA), and the desired concentration of oligomeric compound (either 1 uM or 4 uM). Untreated cells served as a control. After 48 hours, RNA was isolated from the cells and target mRNA levels were measured by real-time PCR. A concentration-dependent reduction in target mRNA was observed, demonstrating that the oligomeric compounds were internalized by MHT cells, and that the oligomeric compound was able to hybridize to and reduce the level of the target mRNA.

Additional oligomeric compounds having nucleobase sequence complementary to endogenous targets were tested, and were found to reduce target mRNA in a concentration-dependent manner.

Oligomeric compound uptake was also found to occur in a time-dependent manner. An SR-B1 oligo conjugated to a fluorescent moiety was added to the culture medium of MHT cells, without a transfection reagent. Cells were harvested at 2, 4, 6.5, and 24 hours, trypsinized, washed, and prepared for flow cytometry. Fluoresence was measured using a flow cytometer (FACSCALIBUR) to assess the amount of oligomeric compound uptake at each timepoint. The amount of oligomeric compound in cells increased in a time-dependent manner.

It was further observed that oligomeric compounds are capable of entering cells within minutes of addition to the culture medium. An SR-B1 oligo was added to MHT cell culture medium, at varying concentrations, without a transfection reagent. Cells were harvested after 15 minutes, 30 minutes, 1 hour, and 2 hours, and SR-B1 mRNA was measured using real-time PCR. Reduction in SR-B1 occurred as early as 15 minutes following addition of the SR-B1 oligo to the culture medium.

Accordingly, the present invention provides cells useful for assessing uptake of oligomeric compounds. In certain embodiments, the uptake is assessed in the presence of a transfection reagent. In certain embodiments, the update is assessed in the absence of a transfection reagent.

Example 3

Competition Assay To Assess the Relative Uptake of Oligomeric Compounds

In certain embodiments, the invention provides a competition assay useful for assessing the uptake of oligomeric compounds. In certain embodiments, the competition assay is useful for assessing the relative uptake of oligomeric compounds. The competition assay employs a competitor oligomeric compound and a reporter oligomeric compound. In certain embodiments, the concentration of the competitor oligomeric compound remains constant while the concentration of the reporter oligomeric compound is varied.

An oligomeric compound complementary to SR-B1 mRNA (SR-B1 oligo) was used as a reporter oligomeric compound. An oligomeric compound complementary to PTEN (PTEN oligo) was used as a competitor oligomeric compound. Cultured MHT cells were cultured in serum-containing medium.

One MHT culture received increasing concentrations of SR-B1 oligo: 10, 100, 1000, and 10000 nM. One day after addition of the oligonucleotides, RNA was isolated from the cells. Real-time PCR demonstrated that SR-B1 mRNA was reduced in a concentration dependent manner, to 78%, 56%, 35%, and 62% of untreated control mRNA levels, respectively.

Additional cultures received both SR-B1 and PTEN oligos. The cultures received the combinations of SR-B1 and PTEN oligos shown in Table 1. After 24 hours, RNA was isolated from the cells. Real-time PCR was used to measure SR-B1 mRNA levels.

TABLE 1

MHT cell treatments

| SR-B1 oligo | PTEN oligo | SR-B1 mRNA % untreated control |
|---|---|---|
| 100 nM | 0 nM | 62 |
| 100 nM | 80 nM | 59 |
| 100 nM | 400 nM | 72 |
| 100 nM | 2000 nM | 82 |
| 100 nM | 10000 nM | 95 |
| 200 nM | 0 nM | 38 |
| 200 nM | 80 nM | 52 |
| 200 nM | 400 nM | 53 |
| 200 nM | 2000 nM | 75 |
| 200 nM | 10000 nM | 88 |
| 400 nM | 0 nM | 33 |
| 400 nM | 80 nM | 42 |
| 400 nM | 400 nM | 42 |
| 400 nM | 2000 nM | 52 |
| 400 nM | 10000 nM | 78 |
| 800 nM | 0 nM | 34 |
| 800 nM | 80 nM | 41 |
| 800 nM | 400 nM | 41 |
| 800 nM | 2000 nM | 50 |
| 800 nM | 10000 nM | 81 |
| 1600 nM | 0 nM | 31 |
| 1600 nM | 80 nM | 35 |
| 1600 nM | 400 nM | 31 |
| 1600 nM | 2000 nM | 39 |
| 1600 nM | 10000 nM | 67 |

As shown in Table 1, an inverse correlation between PTEN oligo concentration and SR-B1 mRNA levels was observed. While the SR-B1 oligo concentration is held constant and the PTEN oligo concentration increases, SR-B1 mRNA levels increase, indicating that less SR-B1 oligo is available to hybridize to and effect the reduction of SR-B1 mRNA. This demonstrates that the SR-B1 oligo and PTEN oligo are competing for uptake into the cells, in other words, PTEN oligo is entering the cells in place of the SR-B1 oligo. As the PTEN oligo concentration increases, the amount of PTEN oligo internalized by the cells increases, effectively preventing the cells from internalizing SR-B1 oligo. It was observed that the free uptake is saturable.

The competition assay was performed to compare the uptake of oligomeric compound conjugated to a fluorescent moiety to that of unconjugated oligomeric compounds. MHT cells were incubated with 400 nM of SR-B1 oligo and 1, 4, or 16 uM of fluorescein-conjugated SR-B1 oligo for 24 hours. Cells were then trypsinized, and the amount of fluorescein-conjugated SR-B1 oligo was quantitated by flow cytometry (FACSCALIBER instrument). As the concentration of SR-B1 oligo was increased, the amount of fluorescence in each sample decreased, indicating that the unconjugated SR-B1 oligo competed with the fluorescein-conjugated SR-B1 oligo for cellular uptake.

Example 4

Localization of Oligomeric Compounds In Cells

The localization of oligomeric compounds in MHT cells was compared following introduction of oligomeric compounds into the cell culture medium in the presence or absence of a transfection reagent.

Cells were treated with fluorescein-conjugated oligo in the presence or absence of lipofectin. The following day, the cells were washed and then fixed with 4% formaldehyde for 15 minutes. Fluorescence microscopy revealed that, when the oligomeric compound was introduced in the presence of lipofectin, more oligomeric compound was localized to the nucleus, relative to oligomeric compound that was introduced in the absence of lipofectin.

The localization of oligomeric compound was also compared to the localization of LAMP1, a lysosomal marker. MHT cells were incubated with 1 uM of Cy3-conjugated SR-B1 oligo for 24 hours. Cells were then washed with PBS, fixed with 4% formaldehyde for 15 minutes, permeabilized with 0.1% TritonX-100, and then incubated with FITC-conjugated LAMP1 antibody (1:100 dilution) for one hour. Cells were then stained with DAPI and prepared for microscopic analysis. Fluorescence microscopy revealed that the highest concentration of oligomeric compound is localized to cellular structures that are also marked by LAMP1 staining. This assay indicates that the highest concentration of oligomeric compound is co-localized with lysosomes.

Example 5

Comparison of In Vitro And In Vivo Potency

Cultured cells are often used to screen oligomeric compounds for those compounds that are likely to reduce levels of the intended target. The effects of oligomeric compounds on target mRNA levels were compared to the effects of on target mRNA in vivo, to assess the correlation between in vitro and in vivo potency.

MHT cells were treated as described herein with increasing concentrations of SR-B1 oligo or PTEN oligo, in the presence or absence of lipofection. An additional oligomeric compound, targeted to a non-coding RNA, was tested. Each oligomeric compound reduced respective target mRNA levels in a concentration dependent manner.

The same oligomeric compounds were tested in vivo in normal mice. Mice were injected with a single dose of 1.6, 5, 16, or 50 mg/kg of oligomeric compound. Three days following administration of the oligomeric compound, the mice were sacrificed and liver tissue was isolated. RNA was isolated from the liver tissue, and target mRNA levels were quantitated using real-time PCR. The SR-B1 oligo reduced liver SR-B1 mRNA in a concentration-dependent manner. The oligomeric compound targeted to the non-coding RNA likewise reduced RNA levels in a concentration-dependent manner. The PTEN oligo reduced liver PTEN mRNA levels.

The $ED_{50}$ (dose at which 50% reduction is observed in vivo) and $IC_{50}$ (concentration at which 50% reduction is observed in vitro) for each oligomeric compound was calculated. For each oligomeric compound tested, the rank-order potency in vitro, in the presence or absence of a transfection reagent, correlated well with the in vivo potency. These data indicate that MHT cells may be used to identify oligomeric compounds that will exhibit potency in vivo with respect to mRNA reduction.

Example 6

Oligomeric Compound Uptake In the Presence of Excipients

In certain embodiments, the invention further provides excipients that are useful for administration of oligomeric compounds in vivo. The effects of the excipients on the uptake of oligomeric compounds can be assessed in vitro in MHT cells, and the results can be used to identify excipients that may affect oligomeric compound uptake in vivo.

To assess the effects of dextran sulfate on oligomeric compound activity, MHT cells were treated with increasing concentrations of SR-B1 oligo in the presence and absence of dextran sulfate. One sample included no excipient, a second sample was treated with SR-B1 oligo and 1 uM dextran sulfate, and a third sample was treated with SR-B1 oligo and 10 uM dextran sulfate. After 24 hours, SR-B1 mRNA levels were quantitated by real-time PCR. While the lower concentration of dextran sulfate did not affect antisense activity of the oligomeric compound, the higher concentration did interfere with the antisense activity of the SR-B1 oligo.

To determine whether the uptake of oligomeric compound was inhibited by dextran sulfate, MHT cells were incubated with 400 nM of fluorescein-conjugated SR-B1 oligo in the presence of 0.5 uM, 1 uM, 5 uM or 10 uM of dextran sulfate, for a period of 24 hours. Cells were stained with DAPI, fixed and examined by fluorescence microscopy as described herein. As the concentration of dextran sulfate increased, less oligomeric compound was present in the cells. Thus it was observed that dextran sulfate competes for oligomeric compound uptake into cells.

The inhibition of antisense activity in the presence of dextran sulfate supports the hypothesis that a large portion of oligomeric compound is present in cells in a non-functional compartment. For example, the lower concentration of dextran sulfate inhibited oligomeric compound uptake without interfering with antisense activity, indicating that a portion of the oligomeric compound present in the cell is unproductive.

Additional excipient, chloroquine, was tested for its effects on antisense activity. Chloroquine accumulates preferentially in the lysosomes of cells. MHT cells were incubated with increasing concentrations of SR-B1 oligo in the presence or absence of chloroquine. One sample included no excipient, a second sample was treated with SR-B1 oligo and 20 uM chloroquine, and a third sample was treated with SR-B1 oligo and 40 uM chloroquine. After 24 hours, SR-B1 mRNA levels were quantitated by real-time PCR. At each concentration of chloroquine, SR-B1 mRNA levels were not significantly reduced, even at the highest concentration of SR-B1 oligo, indicating that chloroquine does interfere with antisense activity.

An additional excipient, brefeldin A, was tested for its effects on antisense activity. Brefeldin A interferes with anterograde protein transport from the endoplasmic reticulum to the Golgi apparatus by inhibiting transport in the Golgi apparatus, which leads to proteins accumulating inside the endoplasmic reticulum. MHT cells were incubated with increasing concentrations of SR-B1 oligo in the presence or absence of brefeldin A. One sample included no excipient, a second sample was treated with SR-B1 oligo and 2.5 uM brefeldin A, and a third sample was treated with SR-B1 oligo and 5 uM brefeldin A. After 24 hours, SR-B1 mRNA levels were quantitated by real-time PCR. SR-B1 mRNA levels were not significantly reduced following treatment with SR-B1 oligo in combination with brefeldin A, particularly at the higher dose of brefeldin A, indicating that brefeldin A does interfere with antisense activity.

The inhibition of antisense activity in the presence of brefeldin A or chloroquine suggests that cellular uptake of oligomeric compound is facilitated by an 'endocytotic-like' pathway.

The invention claimed is:

1. A method comprising contacting an MHT cell in vitro with an oligomeric compound in the absence of cationic lipid and assessing cellular uptake of the oligomeric compound.

2. The method of claim 1, wherein the method comprises a competition assay.

3. The method of claim 1, wherein the oligomeric compound is a modified oligonucleotide.

4. The method of claim 2, wherein the oligomeric compound is a modified oligonucleotide.

5. The method of claim 1, wherein the oligomeric compound comprises a mixed backbone.

6. The method of claim 2, wherein the oligomeric compound comprises a mixed backbone.

7. The method of claim 1, wherein the oligomeric compound comprises a nucleoside comprising a 2' modification.

8. The method of claim 2, wherein the oligomeric compound comprises a nucleoside comprising a 2' modification.

9. The method of claim 1, wherein the assessing cellular uptake of the oligomeric compound comprises determining oligomeric compound activity.

10. The method of claim 2, wherein the assessing cellular uptake of the oligomeric compound comprises determining oligomeric compound activity.

* * * * *